United States Patent
Matsubayashi et al.

(10) Patent No.: US 10,631,559 B2
(45) Date of Patent: Apr. 28, 2020

(54) ACIDIC EXTRACTS AND BEVERAGES CONTAINING 2,5-PIPERAZINEDIONE,3,6-BIS(PHENYL METHYL)-(3S,6S)-

(75) Inventors: Hideki Matsubayashi, China Square Central (SG); Kenji Yamamoto, Kanagawa (JP); Hiroshi Watanabe, Tokyo (JP)

(73) Assignees: SUNTORY HOLDINGS LIMITED, Osaka (JP); SUNTORY BEVERAGE & FOOD ASIA PTE. LTD., Singapore (SG)

( * ) Notice: Subject to any disclaimer, the term of this patent is extended or adjusted under 35 U.S.C. 154(b) by 0 days.

(21) Appl. No.: 13/518,560

(22) PCT Filed: Feb. 26, 2010

(86) PCT No.: PCT/JP2010/053699
§ 371 (c)(1),
(2), (4) Date: Jul. 20, 2012

(87) PCT Pub. No.: WO2011/077761
PCT Pub. Date: Jun. 30, 2011

(65) Prior Publication Data
US 2012/0282387 A1    Nov. 8, 2012

(30) Foreign Application Priority Data
Dec. 25, 2009   (JP) .................. 2009-296247

(51) Int. Cl.
*A23L 2/52*         (2006.01)
*C07D 241/08*       (2006.01)
(Continued)

(52) U.S. Cl.
CPC ............. *A23L 2/52* (2013.01); *A23L 2/68* (2013.01); *A23L 13/30* (2016.08); *C07D 241/08* (2013.01)

(58) Field of Classification Search
CPC ... A23L 1/313; A23L 2/52; A23L 2/68; C07D 241/08
(Continued)

(56) References Cited

U.S. PATENT DOCUMENTS 4,006,261 A * 2/1977 Pickenhagen ....... A23L 1/22678
                                                    426/537
5,232,732 A * 8/1993 Harris et al. .................. 426/589
(Continued)

FOREIGN PATENT DOCUMENTS

| CN | 101317648 A | * 12/2008 |
| JP | 2003-102436 A | 4/2003 |
| WO | 2011/077760 | 6/2011 |

OTHER PUBLICATIONS

USPTO EIC Search of Dec. 3, 2013.*
(Continued)

*Primary Examiner* — Patricia A George
(74) *Attorney, Agent, or Firm* — Greenblum & Bernstein, P.L.C.

(57) ABSTRACT

The present invention aims to provide extracts available for use in acidic beverage production and containing 2,5-piperazinedione,3,6-bis(phenylmethyl)-,(3S,6S)-, which is a useful substance with an improving effect on learning motivation.
When an acid treatment step is included in the production of extracts containing 2,5-piperazinedione,3,6-bis(phenylmethyl)-,(3S,6S)-, it is possible to obtain acidic extracts which cause no sedimentation even when added to beverages. The extracts of the present invention can be added to beverages and so on without impairing the taste inherent to foods and beverages, and can be used for production of acidic beverages preferred by most consumers.

17 Claims, 2 Drawing Sheets

(51) Int. Cl.
*A23L 2/68* (2006.01)
*A23L 13/30* (2016.01)

(58) Field of Classification Search
USPC .......................................................... 426/590
See application file for complete search history.

(56) References Cited

U.S. PATENT DOCUMENTS

| 6,586,033 | B1* | 7/2003 | Gimelli | A23L 1/221 |
| | | | | 426/589 |
| 2008/0050485 | A1 | 2/2008 | Meyer | |
| 2009/0068281 | A1 | 3/2009 | Toyomura et al. | |
| 2010/0055268 | A1* | 3/2010 | Meyer | 426/326 |
| 2012/0283178 | A1 | 11/2012 | Tsuruoka et al. | |
| 2012/0283270 | A1 | 11/2012 | Matsubayashi et al. | |

OTHER PUBLICATIONS

Grass: http://www.amazon.com/Mrs-Grass-Noodle-Chicken-Broth/dp/B0012272P6; May 2009.*
Chen: Two-step mass spectrometric approach for the identification of diketopiperazines in chicken essence; Eur Food Res Technol (2004) 218:589-597; DOI 10.1007/s00217-004-0901-x; Received: Dec. 8, 2003 / Revised: Jan. 29, 2004 / Published online: Mar. 11, 2004.*
CP: ChemPrime; http://wiki.chemprime.chemeddl.org/index.php/Acid_Value_(AV)_and_the_quality_of_fats_and_oils; printed Jun. 12, 2014.*
MRH: Mountain Rose Herbs; https://www.mountainroseherbs.com/products/olive-oil-organic-extra-virgin/profile; printed Jun. 12, 2014.*
Pippen: Chicken Broth Flavor and pH Poultry Science (1965) 44 (3): 816-824.*
Wiki: Brix; published online at least by May 7, 2005 at: http://web.archive.org/web/20050507103952/http://en.wikipedia.org/wiki/Brix.*
Chemspider: found online on May 11, 2016 at: http://www.chemspider.com/Chemical-Structure.68602.html.*
Higgins: Composition and methods of making frozen infant and toddler food; WO 2009085316 A1; published Jul. 9, 2009; priority date: Dec. 31, 2007.*
Fujita: Foodstuffs for sports, for maintenance and improvement of health, comprises extract of chicken meat; Publication #: JP 2002051730 A; published Feb. 19, 2002. (Year: 2002).*
International Search Report for PCT/JP2010/053699, dated Apr. 27, 2010.
Japanese Office Action issued with respect to patent family member Japanese Patent App. No. 2009-296247, dated Sep. 5, 2011, along with an English-language translation.
Japanese Patent App. No. 2009-296164, filed Dec. 25, 2009.
Australian Office Action issued for Australian Patent Application No. 2010334165, dated Dec. 23, 2014.
Korean Office Action in respect to Korean Application No. 520090174560, dated Nov. 25, 2016.

* cited by examiner

[Fig. 1]
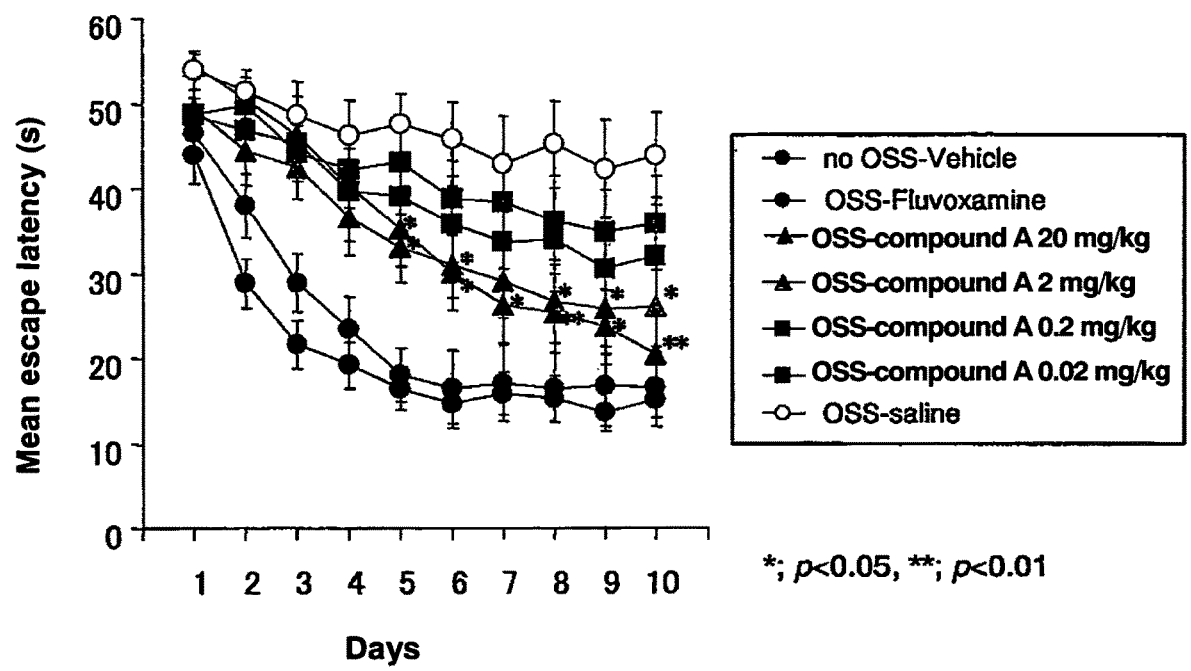
[Fig. 2]
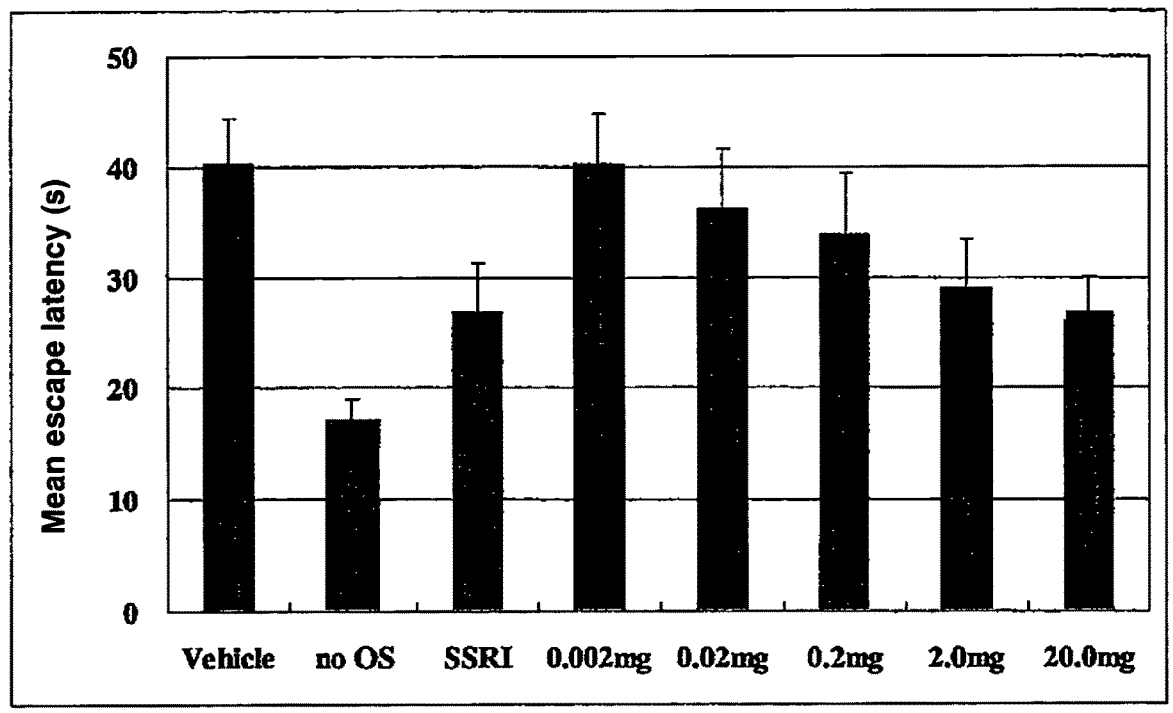

[Fig. 3]
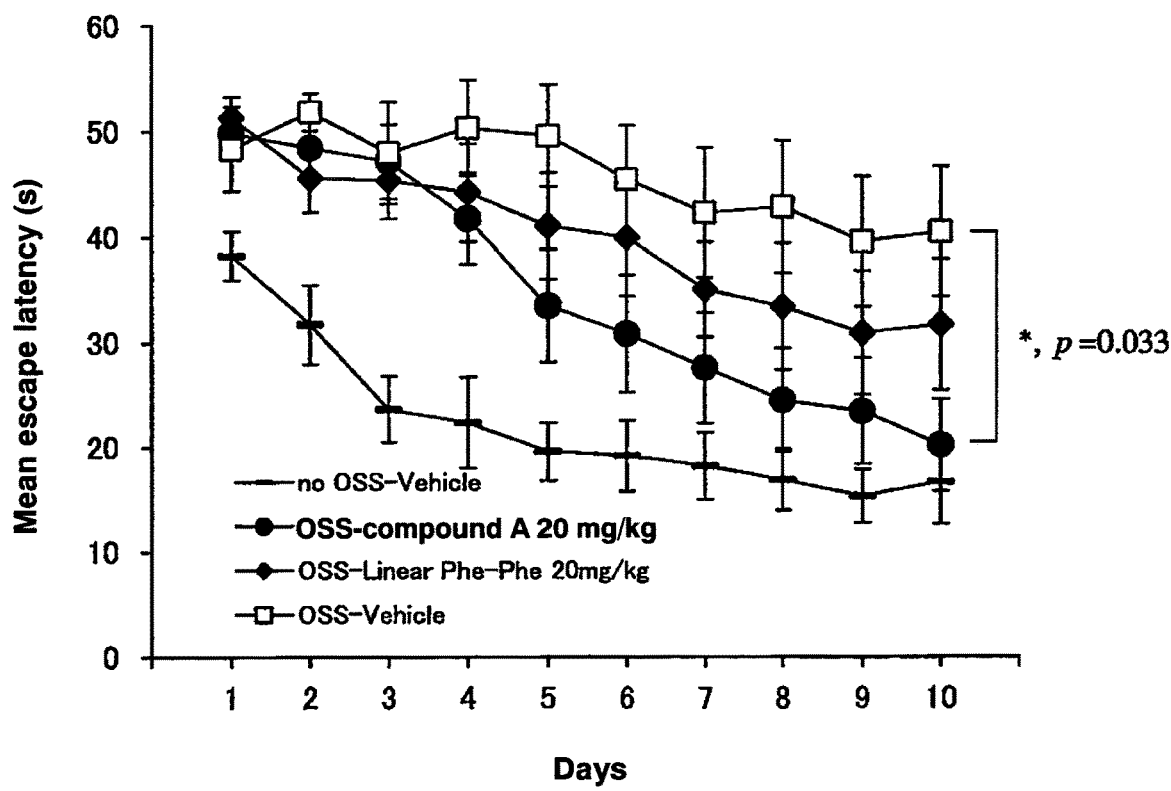
[Fig. 4]
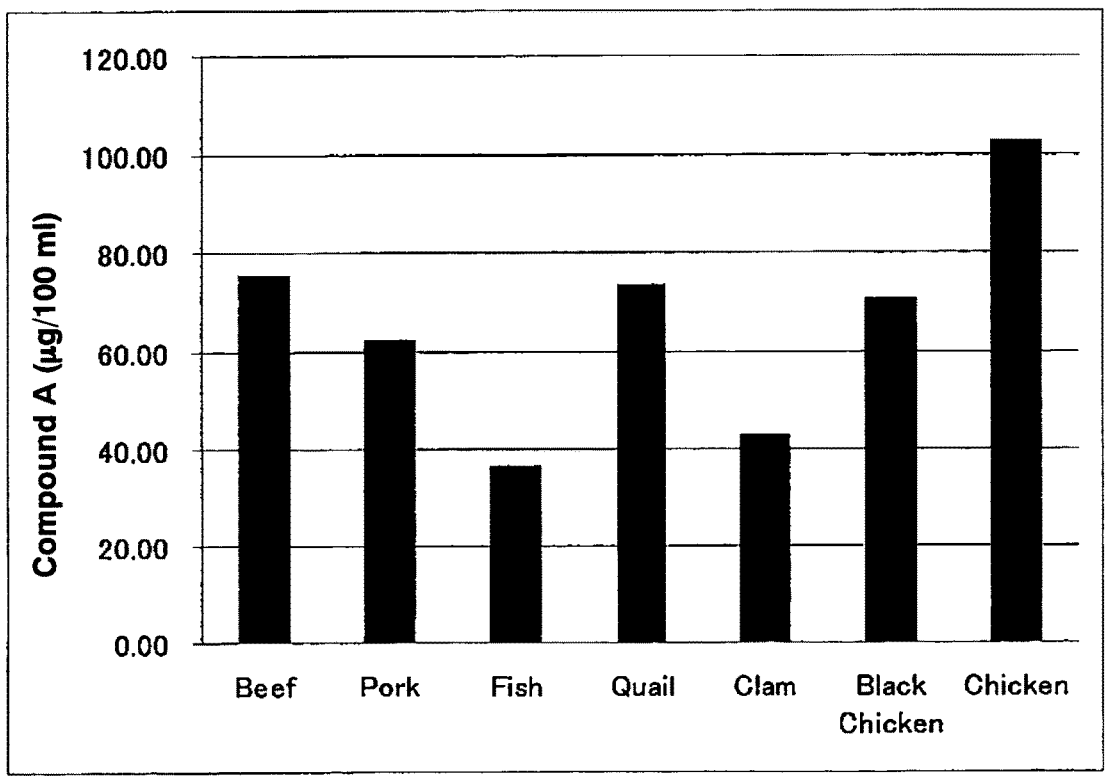

ACIDIC EXTRACTS AND BEVERAGES CONTAINING 2,5-PIPERAZINEDIONE,3,6-BIS(PHENYL METHYL)-(3S,6S)-

TECHNICAL FIELD

The present invention relates to acidic foods and beverages containing 2,5-piperazinedione,3,6-bis(phenylmethyl)-,(3S,6S)-, and more particularly relates to extracts and beverages containing 2,5-piperazinedione,3,6-bis(phenylmethyl)-,(3S,6S)-, wherein the pH is less than 5.

BACKGROUND ART

In a highly complex modern society, a reduction of willingness turns into a problem. For example, the term "motivation crisis" is used to describe the problem of reduced motivation in young people. Moreover, it is said that depression patients often show symptoms of hypobulia, and there is a demand for the development of drugs capable of improving hypobulia.

In recent years, a "dipeptide" composed of two amino acids attached to each other has received attention as a functional substance. Dipeptides can be designed to have additional physical properties and/or new functions, which cannot be seen in single amino acids, and hence they are expected to be applicable to a wider range than that of amino acids. The inventors of the present invention have found that a 2,5-diketopiperazine derivative, i.e., 2,5-piperazinedione, 3,6-bis(phenylmethyl)-,(3S,6S)- (CA Registry Number: 2862-51-3) (hereinafter referred to as "compound A") has an improving effect on learning motivation (the co-filed patent application: Japanese Patent Application No. 2009-296164).

On the other hand, most consumers prefer acidic beverages. Products known to contain compound A include chicken extracts in liquid form which are obtained by decocting meat of livestock, as well as chicken consomme and the like in solid form.

SUMMARY OF INVENTION

Technical Problem

However, products including chicken extract and chicken consomme have a neutral pH. When such a neutral extract is added to an acidic liquid with the aim of providing compound A-containing beverages in the form of acidic beverages which are preferred by most consumers, the extract not only causes sedimentation, but also leaves a taste and slack or grainy feeling on the tongue peculiar to chicken extract, so that satisfactory beverages cannot be obtained in terms of flavor.

Moreover, compound A is hardly soluble in water and hence cannot be simply added as such to beverages.

In view of the foregoing, the present invention aims to provide an extract available for use in acidic beverage production and containing compound A, which is a useful substance with an improving effect on learning motivation, as well as an acidic beverage containing compound A.

Solution to Problem

As a result of extensive and intensive efforts made to solve the problems stated above, the inventors of the present invention have succeeded in obtaining acidic extracts containing compound A, which cause no sedimentation even when added to beverages and which are good in flavor and feeling on the tongue. This success led to the completion of the present invention.

Namely, the present invention is directed to [1] to [20] shown below.

[1] An extract containing compound A and having a pH of less than 5.

[2] The extract according to [1] above, wherein the ratio between the content of compound A (μg/100 g) and Brix (Bx) is 0.1 (μg/100 g)/Bx or more.

[3] The extract according to [1] above, wherein the ratio between the content of compound A (μg/100 g) and Brix (Bx) is 6 (μg/100 g)/Bx or more.

[4] The extract according to any one of [1] to [3] above, which contains compound A at a concentration of 1 μg/100 g or more.

[5] The extract according to any one of [1] to [3] above, which contains compound A at a concentration of 60 μg/100 g or more.

[6] The extract according to any one of [1] to [5] above, wherein compound A is extracted from a naturally occurring product.

[7] The extract according to [6] above, wherein the naturally occurring product is meat of livestock or poultry, fish meat, or shellfish meat.

[8] The extract according to [6] or [7] above, wherein the naturally occurring product is chicken meat.

[9] A dried extract obtainable by drying the extract according to any one of [1] to [8] above.

[10] An acidic beverage obtainable by addition of the extract according to any one of [1] to [8] above.

[11] An acidic beverage containing compound A and having a pH of less than 5.

[12] The acidic beverage according to [10] or [11] above, wherein the ratio between the content of compound A (μg/100 g) and Brix (Bx) is 0.1 (μg/100 g)/Bx or more.

[13] The acidic beverage according to any one of [10] to [12] above, which contains compound A at a concentration of 1 μg/100 g or more.

[14] The acidic beverage according to any one of [10] to [13] above, wherein the beverage is free from sediments.

[15] The acidic beverage according to any one of [10] to [13] above, wherein the beverage contains sediments and wherein the amount of proteins contained in 1 g of the sediments collected from the beverage is 0.01 mg or less.

[16] A packaged beverage, wherein the beverage according to any one of [10] to [15] above is packed in a container.

[17] A process for producing the extract according to [1] above, which comprises:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, (3) an acid treatment step in which an acid is added, and (4) a filtration step in which the obtained liquid sample is filtered.

[18] The process according to [17] above, wherein the acid added in step (3) is one or more members selected from the group consisting of phosphoric acid, malic acid and citric acid.

[19] A process for producing the beverage according to [11] above, which comprises:
(1) a pretreatment step in which meat of livestock or poultry, fish meat or shellfish meat is used as a starting material and heated in a liquid to remove water-soluble proteins contained therein,
(2) a heating step in which the liquid is replaced after the pretreatment and heating is repeated again,
(3) an acid treatment step in which an acid is added, and
(4) a filtration step in which the obtained liquid sample is filtered.

[20] The process according to [19] above, wherein the acid added in step (3) is one or more members selected from the group consisting of phosphoric acid, malic acid and citric acid.

Advantageous Effects of Invention

The present invention provides acidic extracts, which contain compound A having an improving effect on learning motivation and being highly safe without side effects and which cause no sedimentation even when added to beverages. The extracts of the present invention can be added to beverages and so on without impairing the taste inherent to foods and beverages, and can be used for production of acidic beverages preferred by most consumers. The acidic extracts or beverages of the present invention, as well as foods and beverages comprising the same can be ingested continuously over a long period of time as foods and beverages useful for improvement of learning motivation.

BRIEF DESCRIPTION OF DRAWINGS

FIG. 1 shows the test results of whether the ingestion of a test sample reduces the time required for mice to find out an escape platform when repeating the test.

FIG. 2 shows the test results of whether the ingestion of a test sample reduces the time required for mice to find out an escape platform when repeating the test.

FIG. 3 shows the test results of whether the ingestion of a test sample reduces the time required for mice to find out an escape platform when repeating the test.

FIG. 4 shows the quantification results of compound A in extracts obtained with various starting materials.

DESCRIPTION OF EMBODIMENTS

A detailed explanation will be given below for the embodiments of the present invention.

<Acidic Extract>

The acidic extract of the present invention contains compound A, which is a useful substance with an improving effect on learning motivation, and causes no sedimentation even when added to acidic beverages.

The acidic extract of the present invention is also applicable to acidic beverages without causing sedimentation. The acidic extract of the present invention is an extract which allows compound A to be incorporated into beverages at a high concentration while suppressing influences on the overall flavor or feeling on the tongue of the beverages. These characteristics allow greater latitude in flavor design of beverages.

The extract of the present invention is acidic, and the term "acidic" used herein is intended to mean a pH of less than 5. The liquid of the present invention has a pH of less than 5, preferably 4.5 or less, and more preferably 4 or less.

One embodiment of the extract of the present invention is an extract which has a pH of less than 5 and contains compound A at a high concentration, and whose ratio between the content of compound A (µg/100 g) and Brix (Bx) is 0.1 or more, preferably 6 (µg/100 g)/Bx or more.

Since compound A is a useful substance with an improving effect on learning motivation, it is more desirable to have a higher content in the extract. More specifically, the content is preferably 1 µg/100 g or more, more preferably 60 µg/100 g or more, and even more preferably 75 µg/100 g or more. However, an extract with a high Brix value means that various substances (e.g., bitter components) originating from starting materials are contained at high concentrations, and such an extract is in itself unsuitable as a beverage and also affects the flavor or feeling on the tongue so greatly that it is often unsuitable for use in beverages. Thus, a lower Brix value is more desirable for the extract. It should be noted that "Bx" used herein can be determined with a commercially available Bx meter.

Thus, preferred is an extract being rich in compound A, which is a useful substance, and having a low Brix value, i.e., an extract whose ratio between the content of compound A (µg/100 g) and Brix (Bx) is high. More specifically, the ratio between the content of compound A (µg/100 g) and Brix (Bx) is preferably 0.1 (µg/100 g)/Bx or more, more preferably 6 or more, and even more preferably 10 or more. Such an extract is advantageous in that it can be incorporated in small amounts into beverages and allows more latitude in beverage design because of its relatively low Bx value although it contains compound A at a high content. As a result, it is possible to prepare beverages which are excellent in appearance (causing no sedimentation or turbidity) and whose flavor is not impaired.

The concentration of compound A can be quantified in various manners, for example, by high performance liquid chromatography (HPLC).

The acidic extract of the present invention is a liquid extract, which may be ingested as such or may be added to foods and beverages. In addition, the extract can be easily converted into a powder form through a step of lyophilization or freeze-drying, etc. The resulting extract powder is water-soluble and can be easily dissolved in a liquid (e.g., water) before ingestion. Moreover, conversion into a powder form facilitates addition of the extract to various foods and beverages, and allows easy use of the extract.

Alternatively, the form of soft capsules or tablets is also possible. Soft capsules or tablets encapsulate the extract of the present invention, or an extract powder or granule thereof.

There is no limitation on the type or form of foods and beverages into which the extract or extract powder is incorporated. For example, they can be provided in the form of health foods in a tablet form (e.g., tablets and capsules), solid foods including yogurt, processed foods, desserts and sweets (e.g., gum, candy, jelly), liquid beverages including coffee, oolong tea, tea, soft drinks and drinkable preparations. Moreover, pet foods and animal feeds are also included.

<Acidic Beverage>

The present invention is directed to an acidic beverage containing compound A and having a pH of less than 5. One embodiment of the present invention is a beverage containing compound A and having a pH of less than 5, wherein the ratio of the compound A content/Bx is 0.1 (µg/100 g)/Bx or more.

Since compound A is a useful substance with an improving effect on learning motivation, it is more desirable to have a higher content in the beverage. More specifically, the content is preferably 1 µg/100 g or more, more preferably 60 µg/100 g or more, and even more preferably 75 µg/100 g or more.

In contrast to the content of compound A for which a higher value is more desirable, a lower value is more desirable for Brix because beverages with high Brix values are not preferred in terms of flavor and feeling on the tongue, etc. Thus, preferred is a beverage being rich in compound A, which is a useful substance, and having a low Brix value, i.e., a beverage whose ratio between the content of compound A (µg/100 g) and Brix (Bx) is high. More specifically, the ratio between the content of compound A (µg/100 g) and Brix (Bx) is preferably 0.1 (µg/100 g)/Bx or more, more preferably 6 or more, and even more preferably 10 or more.

The beverage of the present invention is characterized not only in that it has an improving effect on learning motivation and can be ingested continuously over a long period of time, but also in that it is good in flavor and feeling on the tongue and further has a good appearance. Particularly in the case of beverages prepared using the extract of the present invention mentioned above, sediments originating from the extract are not generated upon addition of the extract to the beverages although compound A is contained at a high content. Thus, the resulting beverages are characterized in that they are free from sediments originating from the extract. Liquids into which the extract is to be incorporated include those which are themselves free from sediments (e.g., beverages based on transparent fruit juice, as exemplified by apple juice beverages based on transparent fruit juice) and those which themselves contain sediments (e.g., beverages based on cloudy fruit juice, as exemplified by orange juice beverages based on cloudy fruit juice). In the case of beverages prepared by adding the extract of the present invention to a liquid free from sediment components, the resulting beverages are also free from sediments. On the other hand, in the case of beverages prepared by adding the extract of the present invention to a beverage which itself contains sediment components (e.g., a beverage based on cloudy fruit juice), the resulting beverages contain sediments originating from the cloudy fruit juice, but are substantially free from sediments originating from the extract of the present invention.

In beverages prepared by adding the extract of the present invention to a liquid free from sediment components, the presence or absence of sedimentation may be confirmed, for example, visually or by the fact that no solid matter is collected by centrifugation.

On the other hand, in beverages prepared by adding the extract of the present invention to a beverage which itself contains sediment components (e.g., an orange juice-based beverage), to confirm whether they are substantially free from sediments originating from the extract of the present invention, for example, sediments in the beverages may be collected and analyzed to identify whether the sediments have very small amounts of proteins which are solubilized with a surfactant such as sodium dodecyl sulfate (hereinafter referred to as "SDS"). If the beverages contain sediments of the components originating from the extract, proteins originating from the extract are solubilized by treatment with the surfactant. In contrast, if the beverages are substantially free from sediments originating from the extract, there are only very small amounts of proteins to be solubilized. It should be noted that protein solubilization with SDS may be accomplished in a manner well known to those skilled in the art, for example, by using a 0.025% SDS solution. In this case, the result that there are only very small amounts of proteins to be solubilized is intended to mean that the amount of proteins solubilized with a 0.025% SDS solution is not substantially included in the solid content (wet weight) of sediments (i.e., 0.01 mg/g of sediments or less, preferably 0.001 mg/g of sediments or less).

As used herein, the solid content (wet weight) of sediments is intended to mean the weight of solid matter in a wet state, which is collected from a beverage by centrifugation in a centrifugal separator at 3000 to 5000 rpm for 1 to 5 minutes.

The beverage of the present invention has a pH of less than 5, preferably 4.5 or less, and more preferably 4 or less.

The beverage of the present invention can be provided in the form of a packaged beverage, as in the case of conventional beverages.

<Production Process for Extract or Beverage>

The present invention is directed to an acidic extract or beverage containing compound A. Such an extract or beverage can be prepared, for example, by the production process shown below:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, (3) an acid treatment step in which an acid is added, and (4) a filtration step in which the obtained liquid sample is filtered.

A preferred starting material used in the above pretreatment step (1) is a naturally occurring product from which compound A, a useful component, can be efficiently obtained, particularly meat of livestock or poultry, fish meat, or shellfish meat. Examples of meat of livestock or poultry include meat of livestock, i.e., cattle, pig, horse, sheep or goat, meat of non-livestock animals such as wild boar or deer, meat of poultry, i.e., chicken, turkey, quail, domestic duck or crossbred duck, as well as meat of non-poultry wild birds such as wild duck, pheasant, sparrow or thrush. Likewise, it is also possible to use fish meat and shellfish meat which are eaten in the course of a normal diet. As other examples, plant materials such as coffee and cocoa can also be used. Among these examples for meat of livestock or poultry, fish meat and shellfish meat, chicken meat is preferred for use because compound A can be efficiently obtained at a high concentration.

Although the reason why compound A is obtained in large amounts when using chicken meat is unknown, it is inferred that proteins in chicken meat are rich in the contiguous phenylalanine (-Phe-Phe-) structure and thereby generate a dipeptide (Phe-Phe) in abundance, as a result of which compound A of interest will be obtained in large amounts.

In the pretreatment step (1), any treatment for reducing water-soluble proteins contained in a starting material may be performed, for example, by boiling in water at 100° C. to 160° C. for 30 minutes to several hours (preferably 3 to 8 hours, more preferably about 3 to 4 hours). As a heating device, a pressure cooker, an autoclave and so on can be combined for use depending on the intended conditions. Moreover, there is no limitation on the number of liquid replacements performed in the pretreatment step (1). For example, during the step (1), an additional liquid (e.g., water) or an additional starting material may further be added to adjust the concentration of an extract or beverage.

The heating step (2) is preferably accomplished at a high temperature under a high pressure (100° C. or more and 1 atm or more), for example, at 100° C. or more, and more preferably at 125° C. or more. In addition, the heating time in the heating step (2) preferably ranges from 30 minutes to several hours, more preferably from about 3 to 7 hours. As a heating device, a pressure cooker, an autoclave and so on can also be combined for use depending on the intended conditions.

The pretreatment step (1) and the heating step (2) may be performed continuously as a single step without liquid replacement. Alternatively, the pretreatment step may be followed by removal of the pre-treated meat and then replacement of the liquid before the meat is subjected to the heating step. Since samples with lower Brix values can be obtained when liquid replacement is performed after the pretreatment step (1) and before the heating step (2), it is more desirable to use liquid replacement.

It should be noted that heat treatment in the steps (1) and (2) is preferably performed in a solvent in order to prevent plant and animal materials from burning. Examples of a solvent preferred for use include water, ethanol, or mixtures thereof. Namely, a plant or animal material containing proteins (preferably proteins rich in the contiguous phenylalanine (-Phe-Phe-) structure) is mixed with a solvent and subjected to heat treatment, followed by collection of the solvent to obtain a solution rich in compound A.

To ensure a state where a liquid (extract) containing compound A is free from sediments under acidic conditions or a state where an acidic beverage obtained by addition of the extract is free from sediments, acid treatment should be performed to acidify the compound A-containing product obtained in the step (2). This acid treatment is preferably performed following the step (2). Any acid may be added for this purpose, and preferred are food additives and food starting materials commonly used in food production. Examples of food additives include adipic acid, citric acid, lactic acid, acetic acid, glucono-delta-lactone, fumaric acid, gluconic acid, glacial acetic acid, malic acid, tartaric acid, phosphoric acid, L-ascorbic acid and so on. Likewise, examples of food starting materials include itaconic acid, phytic acid, α-ketoglutaric acid, ume vinegar, grain vinegar, fruit juice, malt vinegar, grape vinegar, apple vinegar, rice vinegar and so on. Although any acid may be used as long as it is commonly used in food production, preferred are malic acid, citric acid and phosphoric acid, which are excellent in flavor. These acids may be used either alone or in combination, without any limitation.

Such an acid should be added in an amount required to adjust the pH to a desired value, which may be determined as appropriate depending on the type of acid to be added and the desired pH value.

The power of filtration in the filtration step may be selected as appropriate, depending on the form of foods into which the resulting extract is incorporated, and the filtration method may also be determined as appropriate by those skilled in the art. For example, in cases where the extract is used for solid foods (e.g., tablets) and where the resulting beverages do not need to be clear (e.g., canned beverages whose appearance is hidden in containers), it is sufficient to filter off the sediments generated in the preceding heating step and filtration through a strainer may be used for this purpose. Alternatively, in a case where the extract needs to be clear (e.g., used for beverages in transparent bottles or plastic bottles), powerful filtration should be used. For clarification purposes, filtration through a strainer may be followed by filtration through a membrane (ion exchange membrane, RO membrane, zeta potential membrane, UF membrane) and/or filtration through diatomaceous earth, etc.

In the extract or beverage of the present invention, this solution rich in compound A may be used directly or, if necessary, may be concentrated to further increase the concentration of compound A. Concentration may be accomplished by using an evaporator or by lyophilization, etc.

The content of compound A increases before and after concentration, whereas the ratio between the content of compound A (unit: μg/100 g) and Brix (Bx) remains substantially unchanged. This is because the Brix value also increases upon concentration. Thus, when samples whose ratio between the content of compound A (unit: μg/100 g) and Brix (Bx) is 6 or more are concentrated, it is possible to obtain extracts containing a higher content of compound A and having a ratio of 6 or more. In contrast, when samples whose ratio between the content of compound A (unit: μg/100 g) and Brix (Bx) is less than 6 are concentrated, it is not possible to obtain extracts whose ratio between the content of compound A (unit: μg/100 g) and Brix (Bx) is 6 or more, although extracts containing a high content of compound A are obtained.

The beverage of the present invention may be provided as appropriate in the form of a packaged beverage, when needed.

The present invention will be further described in more detail by way of the following examples, which are not intended to limit the present invention.

EXAMPLES

<Example 1> Improving Effect of Compound A on Learning Motivation (1)

Compound A was evaluated for its enhancing effect on learning motivation by the method known in the art, i.e., Morris Water Maze (MWM).

First, water which had been colored black with Indian ink was filled into a cylindrical tank of 90 cm diameter and 35 cm height to give a water depth of 20 cm, and the water temperature was set to 22±1° C. To this tank, C57BL/6 mice (male, 9 weeks of age) were each transferred and allowed to experience open space swimming (OSS). Upon OSS, mice will cause changes in their behavior and enter a state corresponding to depression. After repeating OSS for 5 days, the mice were divided into 7 groups.

Next, in the above cylindrical tank of 90 cm diameter and 35 cm height, an escape platform of 10 cm diameter was placed at a water depth of 0.5 cm. The above 7 groups of mice were each orally administered with compound A (Bachem AG (Bubendorf, Switzerland)) or with a comparative drug, fluvoxamine maleate. After 60 minutes, each mouse was transferred to the tank provided with the escape platform, and measured for the time required to find out the invisible escape platform placed below the water surface (i.e., escape latency) to evaluate the spatial memory and learning ability of each mouse (MWM). As control mice, animals experiencing no OSS were administered with physiological saline and subjected to MWM. MWM was repeated five times a day for 10 days.

The results obtained are shown in FIG. 1. As can be seen from FIG. 1, in the mice experiencing no OSS (no OSS-Vehicle), the escape latency was reduced when repeating the test, whereas the mice experiencing OSS showed reduced learning motivation and there was no reduction in the escape latency (OSS-Saline). In contrast, the group receiving compound A showed a dose-dependent reduction in the escape latency. In the 0.02 mg/kg group, the escape latency at 10 days of MWM was reduced by around 20%, when compared to the control group (OSS-Saline) in which animals experiencing OSS were administered with physiological saline. Moreover, in the 20 mg/kg group, the time required to reach the escape platform at 10 days of MWM was substantially the same as that of the group (OSS-Fluvoxamine) receiving fluvoxamine maleate, which is frequently used as SSRI. This indicates that compound A has an enhancing effect on learning motivation.

<Example 2> Improving Effect on Learning Motivation (2)

In the same manner as shown in Example 1, another group receiving 0.002 mg/kg administration was prepared and subjected to the same MWM test.

The time required to reach the escape platform at 7 days of MWM is shown in FIG. 2 for each group. Compound A was confirmed to exert its effect when administered at 0.02 mg/kg or more. In a case where the dose for humans is predicted from the effective dose in animals, the human dose is calculated to be 1/10 of the mouse dose with a coefficient of 10 based on animal species specificity (Safety Assessment of Foods, edited by Kageaki Aibara and Mitsuru Uchiyama, Japan Scientific Societies Press, 1987). Thus, 0.02 mg/kg which was effective in the above test corresponds to 0.1 mg/human (50 kg). If compound A-containing foods are prepared in the form of beverages and their volume is set to 100 ml, their effective concentration is calculated to be 1.0 µg/ml.

<Example 3> Improving Effect on Learning Motivation (3)

In the same manner as shown in Example 1, mice were administered with 20 mg/kg compound A and then subjected to the MWM test. As a control, a linear dipeptide (Phe-Phe) was administered at 20 mg/kg, followed by the MWM test.

The results obtained are shown in FIG. 3. As can be seen from FIG. 3, the linear dipeptide (Phe-Phe) was not confirmed to have a significant effect, whereas compound A showed a significant improving effect on learning motivation over the control group (OSS-Saline). Namely, it is indicated that the cyclic dipeptide structure is required for exerting an improving effect on learning motivation.

<Example 4> Study on Starting Materials

As protein-containing starting materials, beef meat, pork meat, fish, quail meat, corbicula clam and chicken meat (Black Chicken, Chicken) were used. Each animal material was mixed with one volume of water and introduced into a container, followed by heat treatment in an autoclave at 135° C. for 4 hours (as a pretreatment step) and further at 135° C. for 4 hours (as a heating step). The heat-treated liquid was collected and adjusted to pH 3 with 75% phosphoric acid for food additive (Nippon Chemical Industrial Co., Ltd., Japan). Then, the liquid was eluted with acetonitrile from a pretreatment column (OASIS MAX (Waters: 30 mg/1 cc)), followed by high performance liquid chromatography (HPLC) to quantify the content of compound A. Conditions for HPLC are as shown below. The results obtained are shown in FIG. 4.

(HPLC Conditions)
System: Agilent 1100 series
Column: Develosil C30-UG-5 (4.6×150 mm, 5 µm)
Mobile phase A: water, Mobile phase B: 100% acetonitrile solution

|  | Time (min) | Solvent B |
|---|---|---|
| Gradient: | 0.00 | 20% |
|  | 9.00 | 20% |
|  | 23.00 | 28% |
|  | 24.00 | 70% |
|  | 31.00 | 70% |
|  | 31.10 | 20% |
|  | 40.00 | 20% |

Injection volume: 10 µl
UV detector wavelength: 215 nm
Flow rate: 1.0 ml/min
Column temperature: 32° C.

It should be noted that a compound A-containing liquid can also be collected from roasted coffee beans themselves, whereas compound A was not detected in coffee beverages extracted from roasted beans.

<Example 5> Production of Compound A-Containing Acidic Extracts (1) As a pretreatment step for removing water-soluble proteins, chicken meat (200 g) and water (200 g) were introduced into a column in a system and treated at a high temperature under a high pressure with a 400 cc high-temperature high-pressure reactor (AKIKO).

(2) Then, as a heating step, the liquid in the above vessel was isolated and discarded. Water was added in an amount equal to the mass of the chicken meat, and the same treatment as shown in (1) was repeated again at a high temperature under a high pressure.

(3) The resulting liquid was filtered through a strainer of about 40 mesh. Then, the filtrate was adjusted to pH 3 with an acid for food additive (e.g., phosphoric acid, citric acid, malic acid) and then centrifuged (6500 rpm, 5 minutes) and further filtered through a strainer (300 mesh), followed by filtration through a 5 µm filter (Sumitomo 3M Limited, Japan).

It should be noted that extract 1 in Table 1 below was not subjected to the pretreatment step.

The pH, the content of compound A and the Bx value were measured for each extract to calculate the ratio of compound A content/Bx.

For determination of Bx values, a Bx meter (RX-5000α: Atago Co., Ltd., Japan) was used for measurement.

The results in Table 1 indicate that when the pretreatment step (1) is performed to remove water-soluble proteins or when pretreatment conditions are set to a higher temperature and a longer time, the extracts obtained in the heating step (2) have lower Bx values. As a result, it is indicated that extracts with a high ratio between the content of compound A (µg/100 g) and Brix (Bx) are obtained.

TABLE 1

|  | Extract | | | | |
| --- | --- | --- | --- | --- | --- |
|  | 1 | 2 | 3 | 4 | 5 |
| Pretreatment step |  | 160° C. 3 hours | 160° C. 6 hours | 160° C. 9 hours | 160° C. 12 hours |
| Heating step | 160° C. 3 hours | 160° C. 3 hours | 160° C. 3 hours | 160° C. 3 hours | 160° C. 3 hours |
| Volume of acid added (per 100 ml of extract) | Phosphoric acid 2.0 ml | Phosphoric acid 0.70 ml | Phosphoric acid 0.20 ml | Phosphoric acid 0.14 ml | Phosphoric acid 0.07 ml |
| Compound A content (μg/100 g) | 135.7 | 139.8 | 111.7 | 112.5 | 108.3 |
| Bx | 12.58 | 4.28 | 1.42 | 0.79 | 0.62 |
| Ratio | 10.8 | 32.7 | 78.7 | 142.4 | 174.6 |
| pH | 3.1 | 3.1 | 3.1 | 2.9 | 3.1 |

<Example 6> Confirmation of the Presence or Absence of Sedimentation Upon Addition of Acidic Extract Chicken extract or consomme of neutral pH or an acidic extract (1 g) was added to liquids (100 g each), which had been adjusted to various pH values with citric acid and 3Na citrate, to study the presence or absence of sedimentation.

As a result, neutral products such as commercially available chicken extract and consomme were found to cause sedimentation when added to acidic liquids. It should be noted that the consomme was dissolved in water before use, as indicated on the package label (150 ml water per 3.55 g of consomme cube).

In contrast, the acidic extract of the present invention was found to be stable without causing sedimentation even when added to acidic liquids.

In the table, "○" indicates that the extract added to the liquid was dissolved and hence caused no sedimentation, while "×" indicates that the extract added to the liquid was not dissolved and hence caused sedimentation.

TABLE 2

|  | Commercially available chicken extract (New Moon) | Consomme (Ajinomoto's chicken consomme cube) | Extract 4 of Example 5 |
| --- | --- | --- | --- |
| pH = 7 | ○ | ○ | ○ |
| pH = 6 | ○ | ○ | ○ |
| pH = 5 | ○ | ○ | ○ |
| pH = 4 | × | × | ○ |
| pH = 3 | × | × | ○ |

<Example 7> Confirmation of Sedimentation (1)

(Sample Preparation)

For mixtures (i) and (ii) shown below, samples were prepared to have the compound A contents and the Brix values shown in Recipe Nos. 1 to 6 of Table 3. For mixture (iii), samples were prepared to have the compound A contents and the Brix values shown in Recipe Nos. 1 to 9 of Table 3. For juice (iv), samples were adjusted by being diluted as appropriate to have the same Brix values as shown in Recipe Nos. 1 to 9 of Table 3. The juice (iv) does not contain compound A, and the ratio of compound A content/Bx is 0 in each sample.

The samples of mixtures (i) to (iii) and juice (iv) prepared above were sterilized at 85° C. for 10 minutes.

The commercially available chicken extract used in this experiment has a Brix value of 10 and a pH of 6.3, and contains 45 μg compound A per 100 g of the extract. Similarly, the commercially available chicken powder used in this experiment is a powder form of the commercially available chicken extract, and contains 45 μg compound A per 10 g of the powder. The acidic extract of the present invention has a Brix value of 61.1 and a pH of 2.55, and contains 48 μg compound A per 1 g of the acidic extract. The apple juice used in this experiment was a clear fruit drink of pH 3.8.

It should be noted that since the ratio of compound A content/Bx is 4.5 (μg/100 g)/Bx in the commercially available chicken extract, for the mixture (i) based on this chicken extract, samples whose ratio of compound A content/Bx is higher than 4.5 (μg/100 g)/Bx cannot be prepared. Thus, only the samples shown in Recipe Nos. 1 to 6 of Table 3 can be prepared. Similarly, in the case of the mixture (ii) based on a powder form of the commercially available chicken extract, only the samples shown in Recipe Nos. 1 to 6 of Table 3 can be prepared. Thus, the mixtures (i) and (ii) cannot be studied for the conditions shown in 7, 8 or 9, and hence are studied only for the conditions shown in 1 to 6.

(i) A mixture of commercially available chicken extract and 100% apple juice
(ii) A mixture of commercially available extract powder and 100% apple juice
(iii) A mixture of the acidic extract of the present invention and 100% apple juice
(iv) 100% Apple juice (control)

(Confirmation of Sedimentation and Feeling on the Tongue)

The above sterilized samples were allowed to stand and confirmed for the presence or absence of sedimentation by visual inspection and for the feeling on the tongue. The results obtained are shown in "Sedimentation" and "Feeling on the tongue" in Table 4.

In the table, "×" indicates that sedimentation cannot be observed visually, while "○" indicates that sedimentation can be observed visually.

The feeling on the tongue was evaluated on a five-point scale in comparison with control samples (commercially available apple juice adjusted to have the same Bx values as shown in Recipe Nos. 1 to 9 by dilution with water):

5=having the same smoothness as that of the control
4=leaving a slightly more grainy feeling on the tongue as compared to the control
3=leaving a relatively more grainy feeling on the tongue as compared to the control 2=leaving a more grainy feeling on the tongue as compared to the control 1=leaving a distinct grainy feeling on the tongue as compared to the control (Measurement of Solid Content and Protein Concentration)

1. Each sample prepared above (20 g) was centrifuged (4000 rpm, 1 minute) to remove the liquid fraction, and the resulting sediments (i.e., solid matter) were collected and measured for their weight.
2. The solid matter obtained in 1 was taken in an amount of 0.05 g, and 200 µl of 0.025% SDS (Sigma Catalogue #L3771) was added thereto.
3. The sample prepared in 2 was vortexed and then centrifuged (14,000 rpm, 1 minute).
4. The supernatant obtained in 3 was taken in a volume of 20 µl and mixed with 1 ml of Bradford reagent (BIO-RAD Catalog #500-0205) at room temperature.
5. The solution prepared in 4 was reacted at room temperature for 5 minutes or more, and then measured for the absorbance at 595 nm with a spectrophotometer (UV-1601 UV-VISIBLE SPECTROPHOTOMETER SHIMADZU).
6. The absorbance value obtained in 5 was used to determine the protein concentration according to a calibration curve which had been prepared in advance.
7. The protein concentration obtained in 6 was used to determine the protein amount per 1 g of the sediments.

Table 4 shows data of the solid content determined in 1 ("Solid content g"), the protein concentration determined in 6 ("Protein (mg) in sediments") and the value determined in 7 ("Protein (mg)/g of sediments") for each sample.

It should be noted that the calibration curve used in this experiment was prepared by the procedures shown below.

1. 70 µl of bovine serum albumin (2 mg/ml; BIO-RAD Catalog #500-0206) was mixed with 70 µl of 0.025% SDS to give a 1000 µg/ml solution of bovine serum albumin.
2. The solution obtained in 1. was serially diluted with 70 µl of 0.025% SDS to prepare 750 µg/ml, 500 µg/ml, 250 µg/ml and 125 µg/ml solutions of bovine serum albumin.
3. As a 0 µg/ml solution, 70 µl of 0.025% SDS was used.
4. 20 µl aliquots of the above bovine serum albumin solutions were each mixed with 1 ml of Bradford reagent (BIO-RAD Catalog #500-0205) at room temperature.
5. After reaction with the Bradford reagent at room temperature for 5 minutes or more, the absorbance at 595 nm was measured with a spectrophotometer (UV-1601 UV-VISIBLE SPECTROPHOTOMETER SHIMADZU).
6. The determined absorbance values and the concentrations of the bovine serum albumin solutions were used to prepare a calibration curve.

TABLE 3

| Recipe No. | 1 | 2 | 3 | 4 | 5 | 6 | 7 | 8 | 9 |
|---|---|---|---|---|---|---|---|---|---|
| Compound A | 30 µg | 60 µg | 100 µg | 30 µg | 60 µg | 100 µg | 30 µg | 60 µg | 100 µg |
| Compound A/Bx | 1 | 1 | 1 | 4.5 | 4.5 | 4.5 | 6 | 6 | 6 |
| Bx | 6 | 12 | 20 | 1.33 | 2.66 | 4.44 | 1 | 2 | 3.33 |
| Weight | 500 g | 500 g | 500 g | 500 g | 500 g | 500 g | 500 g | 500 g | 500 g |

TABLE 4

| Sample No. | i-1 | i-2 | i-3 | i-4 | i-5 | i-6 |
|---|---|---|---|---|---|---|
| Sedimentation | ○ | ○ | ○ | ○ | ○ | ○ |
| Feeling on the tongue | 3 | 2 | 2 | 4 | 3 | 3 |
| Solid content g | 0.72 | 1.21 | 1.85 | 0.66 | 1.06 | 1.5 |
| Protein (mg)/g of sediments | 0.27 | 1.53 | 1.36 | 0.88 | 1.34 | 1.48 |
| Protein (mg) in sediments | 0.19 | 1.85 | 2.52 | 0.58 | 1.42 | 2.22 |

| Sample No. | ii-1 | ii-2 | ii-3 | ii-4 | ii-5 | ii-6 |
|---|---|---|---|---|---|---|
| Sedimentation | ○ | ○ | ○ | ○ | ○ | ○ |
| Feeling on the tongue | 2 | 1 | 1 | 3 | 2 | 2 |
| Solid content g | 2.42 | 1.31 | 1.89 | 0.65 | 1.2 | 1.71 |
| Protein (mg)/g of sediments | 0.45 | 1.24 | 1.74 | 0.80 | 1.05 | 1.32 |
| Protein (mg) in sediments | 1.10 | 1.63 | 3.29 | 0.52 | 1.26 | 2.25 |

| Sample No. | iii-1 | iii-2 | iii-3 | iii-4 | iii-5 | iii-6 | iii-7 | iii-8 | iii-9 |
|---|---|---|---|---|---|---|---|---|---|
| Sedimentation | X | X | X | X | X | X | X | X | X |
| Feeling on the tongue | 5 | 5 | 5 | 5 | 5 | 5 | 5 | 5 | 5 |
| Solid content g | 0 | 0 | 0 | 0 | 0 | 0 | 0 | 0 | 0 |
| Protein (mg)/g of sediments | 0 | 0 | 0 | 0 | 0 | 0 | 0 | 0 | 0 |
| Protein (mg) in sediments | 0 | 0 | 0 | 0 | 0 | 0 | 0 | 0 | 0 |

| Sample No. | iv-1 | iv-2 | iv-3 | iv-4 | iv-5 | iv-6 | iv-7 | iv-8 | iv-9 |
|---|---|---|---|---|---|---|---|---|---|
| Sedimentation | X | X | X | X | X | X | X | X | X |
| Feeling on the tongue | 5 | 5 | 5 | 5 | 5 | 5 | 5 | 5 | 5 |
| Solid content g | 0 | 0 | 0 | 0 | 0 | 0 | 0 | 0 | 0 |
| Protein (mg)/g of sediments | 0 | 0 | 0 | 0 | 0 | 0 | 0 | 0 | 0 |
| Protein (mg) in sediments | 0 | 0 | 0 | 0 | 0 | 0 | 0 | 0 | 0 |

<Example 8> Confirmation of Sedimentation (2)

For mixtures (vi) and (vii) shown below, as in the case of Example 7, samples were prepared to have the compound A contents and the Brix values shown in Recipe Nos. 1 to 6 of Table 3. For mixture (viii), samples were prepared to have the compound A contents and the Brix values shown in Recipe Nos. 1 to 9 of Table 3. For juice (ix), samples were adjusted by being diluted as appropriate to have the same Brix values as shown in Recipe Nos. 1 to 9 of Table 3. The juice (ix) does not contain compound A, and the ratio of compound A content/Bx is 0 in each sample.

The samples of mixtures (vi) to (viii) and juice (ix) prepared above were sterilized at 85° C. for 10 minutes.

The commercially available chicken extract used in this experiment has a Brix value of 10 and a pH of 6.3, and contains 45 µg compound A per 100 g of the extract. Similarly, the commercially available chicken powder used in this experiment is a powder form of the commercially available chicken extract, and contains 45 µg compound A per 10 g of the powder. The acidic extract of the present invention has a Brix value of 61.1 and a pH of 2.55, and contains 48 µg compound A per 1 g of the acidic extract. The orange juice used in this experiment was a cloudy fruit drink of pH 3.74.

It should be noted that since the ratio of compound A content/Bx is 4.5 (µg/100 g)/Bx in the commercially available chicken extract, for the mixture (vi) based on this chicken extract, samples whose ratio of compound A content/Bx is higher than 4.5 (µg/100 g)/Bx cannot be prepared. Thus, only the samples shown in Recipe Nos. 1 to 6 of Table 3 can be prepared. Similarly, in the case of the mixture (vii) based on a powder form of the commercially available chicken extract, only the samples shown in Recipe Nos. 1 to 6 of Table 3 can be prepared. Thus, the mixtures (vi) and (vii) cannot be studied for the conditions shown in 7, 8 or 9, and hence are studied only for the conditions shown in 1 to 6.

(vi) A mixture of commercially available chicken extract and 100% orange juice
(vii) A mixture of commercially available extract powder and 100% orange juice
(viii) A mixture of the acidic extract of the present invention and 100% orange juice
(ix) 100% Orange juice (control)

The samples thus prepared were each analyzed in the same manner as shown in Example 7 to confirm the presence or absence of sedimentation, evaluate the feeling on the tongue, and determine the solid content and the protein concentration. The results obtained are shown in Table 5.

TABLE 5

| Sample No. | vi-1 | vi-2 | vi-3 | vi-4 | vi-5 | vi-6 |
|---|---|---|---|---|---|---|
| Sedimentation | ◯ | ◯ | ◯ | ◯ | ◯ | ◯ |
| Feeling on the tongue | 3 | 2 | 2 | 3 | 2 | 2 |
| Solid content g | 1.28 | 2.58 | 3.21 | 0.30 | 0.69 | 1.09 |
| Protein (mg)/g of sediments | 0.09 | 0.86 | 0.62 | 0.60 | 0.85 | 0.97 |
| Protein (mg) in sediments | 0.12 | 2.22 | 1.99 | 0.18 | 0.59 | 1.06 |

| Sample No. | vii-1 | vii-2 | vii-3 | vii-4 | vii-5 | vii-6 |
|---|---|---|---|---|---|---|
| Sedimentation | ◯ | ◯ | ◯ | ◯ | ◯ | ◯ |
| Feeling on the tongue | 3 | 3 | 2 | 3 | 2 | 1 |
| Solid content g | 1.36 | 2.73 | 3.35 | 0.40 | 0.55 | 1.45 |
| Protein (mg)/g of sediments | 0.32 | 0.26 | 1.30 | 1.87 | 2.42 | 3.15 |
| Protein (mg) in sediments | 0.43 | 0.71 | 4.36 | 0.75 | 1.33 | 4.57 |

| Sample No. | viii-1 | viii-2 | viii-3 | viii-4 | viii-5 | viii-6 | viii-7 | viii-8 | viii-9 |
|---|---|---|---|---|---|---|---|---|---|
| Sedimentation | ◯ | ◯ | ◯ | ◯ | ◯ | ◯ | ◯ | ◯ | ◯ |
| Feeling on the tongue | 5 | 5 | 5 | 5 | 5 | 5 | 5 | 5 | 5 |
| Solid content g | 1.57 | 2.47 | 2.83 | 0.53 | 0.49 | 1.08 | 0.44 | 0.63 | 0.83 |
| Protein (mg)/g of sediments | 0.00 | 0.00 | 0.00 | 0.00 | 0.00 | 0.00 | 0.00 | 0.00 | 0.00 |
| Protein (mg) in sediments | 0.00 | 0.00 | 0.00 | 0.00 | 0.00 | 0.00 | 0.00 | 0.00 | 0.00 |

| Sample No. | ix-1 | ix-2 | ix-3 | ix-4 | ix-5 | ix-6 | ix-7 | ix-8 | ix-9 |
|---|---|---|---|---|---|---|---|---|---|
| Sedimentation | ◯ | ◯ | ◯ | ◯ | ◯ | ◯ | ◯ | ◯ | ◯ |
| Feeling on the tongue | 5 | 5 | 5 | 5 | 5 | 5 | 5 | 5 | 5 |
| Solid content g | 1.18 | 2.47 | 2.27 | 0.48 | 0.77 | 1.02 | 0.44 | 0.57 | 0.78 |
| Protein (mg)/g of sediments | 0.00 | 0.00 | 0.00 | 0.00 | 0.00 | 0.00 | 0.00 | 0.00 | 0.00 |
| Protein (mg) in sediments | 0.00 | 0.00 | 0.00 | 0.00 | 0.00 | 0.00 | 0.00 | 0.00 | 0.00 |

<Example 9> Production of Acidic Beverages Containing Compound A (1)

The extract of the present invention was added to prepare a beverage. The recipe used is as shown below.

The acidic extract used was prepared from extract 3 of Example 5 (shown in Table 1) by concentration in an evaporator.

TABLE 6

| Acidic extract | Extract 3 of Example 5 (concentrated) |
|---|---|
| Bx | 61.1 |
| Acidity (g/100 g) | 36.36 |
| pH | 2.55 |
| Compound A (ug/100 g) | 4806 |
| Ratio | 78.7 |

TABLE 7

| Acidic beverage Starting material (per 100 g) | |
|---|---|
| Sugar | 17.2 g |
| Citric acid | 0.21 g |
| 3Na citrate | 0.075 g |
| Flavoring | 150 µl |
| Extract shown above | 1.66 g |
| Water | Adjusted to 100 g |
| Bx | 18.5 |
| Acidity (g/100 g) | 0.66 |
| pH | 2.75 |
| Compound A (ug/100 g) | 85 |
| Ratio | 4.59 |
| Sensory testing | The beverage has no problem because it is free from the flavor, bitterness and unwanted taste originating from meat of livestock or poultry |
| Appearance | Non-cloudy transparent light-brown |

<Example 10> Production of Compound A-Containing Extract Powder

The extract prepared in Example 5 above was lyophilized to prepare an extract powder.

1. The acidic extract (extract 3 of Example 5 (shown in Table 1); 100 g) was taken into a 200 ml recovery flask.
2. This flask was stored in a freezer (−18° C.) for 2 or 3 days until the extract was completely frozen.
3. The flask was mounted on a lyophilizer (LABCONCO, set at −40° C. or less) and lyophilized to complete dryness.

In the above manner, a dried powder was obtained in a yield of 2 g.

INDUSTRIAL APPLICABILITY

The present invention provides acidic extracts and beverages having an improving effect on learning motivation and being highly safe without side effects. The acidic extracts of the present invention can be added to acidic beverages and so on without causing sedimentation and impairing the taste inherent to foods and beverages. The acidic extracts or beverages of the present invention, as well as foods and beverages comprising the same can be ingested continuously over a long period of time as foods and beverages useful for improvement of learning motivation.

The invention claimed is:

1. A liquid extract, comprising:
   1 µg/100 g or more of 2,5-piperazinedione,3,6-bis(phenylmethyl)-,(3S,6S)-;
   a pH of from about 2.55 to less than 5; and
   a Brix (°Bx);
   wherein the ratio of the content of 2,5-piperazinedione, 3,6-bis(phenylmethyl)-, (3S,6S)- (µg/100 g) to the Brix (°Bx) is from 6 to about 174 (µg/100 g)/°Bx.

2. The liquid extract according to claim 1, wherein the content of 2,5-piperazinedione,3,6-bis(phenylmethyl)-,(3S,6S)- is 60 µg/100 g or more.

3. The liquid extract according to claim 1, wherein 2,5-piperazinedione,3,6-bis(phenylmethyl)-,(3S,6S)- is extracted from a naturally occurring product.

4. The liquid extract according to claim 3, wherein the naturally occurring product is meat of livestock or poultry, fish meat, or shellfish meat.

5. The liquid extract according to claim 3, wherein the naturally occurring product is chicken meat.

6. A dried extract obtainable by drying the liquid extract according to claim 1.

7. An acidic beverage obtainable by addition of the liquid extract according to claim 1.

8. The acidic beverage according to claim 7, wherein the ratio is 0.1 (µg/100 g)/° $B_x$ or more.

9. The acidic beverage according to claim 7, wherein the content of 2,5-piperazinedione,3,6-bis(phenylmethyl)-,(3S, 6S)- is 1 µg/100 g or more.

10. The acidic beverage according to claim 7, wherein the beverage is free from sediments.

11. The acidic beverage according to claim 7, wherein the beverage contains sediments, and wherein the amount of proteins contained in 1 g of the sediments collected from the beverage is 0.01 mg or less.

12. A packaged beverage, wherein the beverage according to claim 7 is packed in a container.

13. A process for producing the liquid extract according to claim 1, which comprises:
   (1) a pretreatment step in which meat of livestock or poultry, fish meat or shellfish meat is used as a starting material and heated in a liquid to remove water-soluble proteins contained therein,
   (2) a heating step in which the liquid is replaced after the pretreatment and heating is repeated again,
   (3) an acid treatment step in which an acid is added, and
   (4) a filtration step in which the obtained liquid sample is filtered.

14. The process according to claim 13, wherein the acid added in step (3) is one or more members selected from the group consisting of phosphoric acid, malic acid, and citric acid.

15. A process for producing the beverage according to claim 1, which comprises:
   (1) a pretreatment step in which meat of livestock or poultry, fish meat or shellfish meat is used as a starting material and heated in a liquid to remove water-soluble proteins contained therein,
   (2) a heating step in which the liquid is replaced after the pretreatment and heating is repeated again,
   (3) an acid treatment step in which an acid is added, and
   (4) a filtration step in which the obtained liquid sample is filtered.

16. The process according to claim 15, wherein the acid added in step (3) is one or more members selected from the group consisting of phosphoric acid, malic acid, and citric acid.

17. The liquid extract of claim 1, which has a pH of from about 2.55 to less than 3.

* * * * *